United States Patent [19]

Meyer

[11] Patent Number: 5,208,373
[45] Date of Patent: May 4, 1993

[54] PROCESS FOR THE PREPARATION OF PERFLUOROPOLYETHERACYL FLUORIDES

[75] Inventor: Matthias Meyer, Frankfurt am Main, Fed. Rep. of Germany

[73] Assignee: Hoechst Aktiengesellschaft, Frankfurt am Main, Fed. Rep. of Germany

[21] Appl. No.: 834,382

[22] Filed: Feb. 12, 1992

[30] Foreign Application Priority Data

Feb. 14, 1991 [DE] Fed. Rep. of Germany ....... 4104465

[51] Int. Cl.$^5$ ............................................. C07C 315/00
[52] U.S. Cl. .................................................. 562/851
[58] Field of Search ........................................ 562/851

[56] References Cited

FOREIGN PATENT DOCUMENTS 0154297 9/1985 European Pat. Off. .
1033574 6/1966 United Kingdom .

Primary Examiner—José G. Dees
Assistant Examiner—Joseph M. Conrad, III
Attorney, Agent, or Firm—Connolly & Hutz

[57] ABSTRACT

A process for the preparation of perfluoropolyetheracyl fluorides of formula (I)

$$F_3C(CF_2)_2\text{—}O\text{—}[CF(CF_3)CF_2\text{—}O\text{—}]_nCF(CF_3)COF \quad (I)$$

in which n is an integer from 0-60, wherein hexafluoropropylene oxide is oligomerized in the presence of CsF and a polyethylene glycol dimethyl ether and the reaction mixture thus formed is reacted with at least one of the halogen compounds HCl, HBr, BCl$_3$, PCl$_3$, SCl$_2$ and R$_m$SiCl$_{4-m}$, where m=0, 1, 2 or 3 and R=C$_1$-C$_3$-alkyl or phenyl, dissolved in an aprotic solvent.

6 Claims, No Drawings

PROCESS FOR THE PREPARATION OF PERFLUOROPOLYETHERACYL FLUORIDES

The invention relates to a process for the preparation of perfluoropolyetheracyl fluorides of formula (I)

$$F_3C(CF_2)_2-O-[CF(CF_3)CF_2-O-]_nCF(CF_3)COF \quad (I)$$

in which n is an integer from 0–60, from the crude oligomer of hexafluoropropylene oxide (HFPO).

The oligomerization of HFPO in the presence of CsF and polyethylene glycol dimethyl ethers, in particular tetraethylene glycol dimethyl ether, is described in EP-A-0 154 297. With this process the HFPO crude oligomer is generally obtained in the form of a mixture having a molecular mass distribution of about 300–20,000 g/mol; however, it still contains CsF and considerable amounts of said solvents, which, on subsequent reaction of the HFPO oligomer with elemental fluorine to give perfluorinated polyethers ("end group stabilization"), form byproducts which contaminate the perfluorinated ethers.

A process for separating off tetraethylene glycol dimethyl ether from the HFPO crude oligomer is described on page 18 of EP-A-0 154 297. Following its saponification to perfluoropolyethercarboxylic acids, the latter are freed from tetraethylene glycol dimethyl ether by repeated extraction with diethyl ether. The residual diethyl ether content is separated off by heating the perfluoropolyethercarboxylic acids under reduced pressure. These acids are then "end group stabilized" using elemental fluorine to form perfluoropolyethers.

It has now been found that it is possible to convert the HFPO crude oligomer into pure perfluoropolyetheracyl fluoride free from said solvents. This compound can then be directly converted into perfluoropolyethers using $F_2$. By this means, the laborious saponification of the crude oligomer to perfluoropolyethercarboxylic acids and the subsequent drying thereof are dispensed with.

The subject of the invention is a process for the preparation of perfluoropolyetheracyl fluorides of formula (I)

$$F_3C(CF_2)_2-O-[CF(CF_3)CF_2-O-]_nCF(CF_3)COF \quad (I)$$

in which n is an integer from 0–60, wherein hexafluoropropylene oxide is oligomerized in the presence of CsF and a polyethylene glycol dimethyl ether and the reaction mixture thus formed is reacted with at least one of the halogen compounds HCl, HBr, $BCl_3$, $PCl_3$, $SCl_2$ and $R_mSiCl_{4-m}$, where m=0, 1, 2 or 3 and R=$C_1$-$C_3$-alkyl or phenyl, dissolved in an aprotic solvent.

In general, 1 to 3 mol of the halogen compound are used per mole of CsF in the reaction mixture (crude oligomer) formed during the oligomerization.

Preferred halogen compounds are HCl and $ClSi(CH_3)_3$ (chlorotrimethylsilane).

The aprotic solvent used can be polar or nonpolar; diethyl ether, tetrahydrofuran, tert-butyl methyl ether, acetone, acetonitrile, chloroform, methylene chloride, pentane, hexane, cyclohexane or heptane, in particular cyclohexane or hexane, are preferably used.

The amount of solvent is in general 0.5 to 3, preferably 0.8 to 1.3, parts by volume per part by volume of crude oligomer.

The reaction temperature is in general −40° C. to +80° C.; the reaction is preferably carried out at room temperature or in the region thereof.

The HFPO crude oligomer obtained in accordance with EP-A-0154297 or British Patent No. 1033574 can be used without pre-purification in the process according to the invention. To this end, the solution of the halogen compound in the aprotic solvent is added to the emulsion comprising the oligomer, CsF and the polyethylene glycol dimethyl ether used and the mixture is stirred. The reaction is essentially complete when the turbidity of the mixture caused by precipitating Cs salt no longer increases. In general, the minimum period is about 30 minutes. A more accurate control of the degree of conversion is possible by means of $^{19}$F-NMR analysis of samples during the reaction.

After filtration, the lower phase also contains, in addition to the desired acyl fluoride (I), about 5,000–10,000 ppm of the solvent used, which, for example, is separated off by means of thin-film distillation. The upper phase contains the bulk of the solvent used and the polyethylene glycol dimethyl ether used for the oligomerization of the HFPO.

The resulting products (I) are obtained in the form of clear, colorless liquids which have a higher or lower viscosity depending on the molecular mass and are sensitive to hydrolysis and which can be converted by reaction with elemental fluorine into the "end group stabilized" perfluoroethers $F_3C(CF_2)_2-O-[CF(CF_3)CF_2-O-]_nCF_2-CF_3$.

The degree of polymerization n of the perfluoropolyetheracyl fluorides can be controlled by means of the temperature during the oligomerization of the HFPO; the lower the temperature chosen the higher the value of n. Values of n=10 to n=60 are of particular interest. However, a mixture of HFPO oligomers of different chain lengths, and therefore a mixture of corresponding acyl fluorides (I), is always formed.

The perfluoropolyethers prepared from the acyl fluorides are used, for example, in the electronics industry and the chemical industry as inert fluids and lubricants.

EXAMPLES

Experimental report (Preparation of the HFPO oligomer)

A solution of 20 g of CsF in 50 ml of tetraethylene glycol dimethyl ether (tetraglyme) and 56 g of hexafluoropropylene oxide were initially introduced under a nitrogen atmosphere into a 4 l V-4-A autoclave. 250 ml of ®Frigen F 113 ($CCl_2F-CF_2Cl$) were additionally added for dilution. 4000 g of hexafluoropropylene oxide were then passed in at a temperature of −40° C. to 0° C. over a period of 8 hours, with good mixing. After the end of the reaction, the reaction mixture was warmed to room temperature and the HFPO crude oligomer was then drained off under a nitrogen atmosphere. This crude oligomer was used in the following examples.

EXAMPLE 1

200 g of the HFPO crude oligomer contaminated with F 113, CsF and tetraglyme were introduced into a 250 ml stirred round-bottom flask. The crude oligomer, which had an average molecular weight of 9700 g/mol, was stirred with a solution of 2 g of chlorotrimethylsilane in 100 ml of diethyl ether at room temperature under a nitrogen atmosphere for 30 minutes. After phase separation, the lower phase containing the product (I) was drained off and filtered to remove cesium chloride, and F 113 and the (low) diethyl ether content were stripped off under vacuum ($10^{-2}$ mbar) at 100° C. 183 g of perfluoropolyetheracyl fluoride (I) (98.9% yield) were obtained. Residual amounts of 0.008% by weight of diethyl ether and 0.002% by weight of tetraglyme were detected in the product (I) using $^1$H-NMR residual proton analysis. The degree of purity of (I) was 99.99%.

EXAMPLE 2

The procedure was as in Example 1, but using 100 ml of tetrahydrofuran instead of diethyl ether.

Using $^1$H-NMR residual proton analysis it was possible to detect residual amounts of 0.1 mg of THF and 0.04 mg of tetraglyme per g of product (I). The yield was 184.3 g, i.e. 99.6%.

EXAMPLE 3

The procedure was as in Example 1, but using 100 ml of n-hexane instead of diethyl ether. Using NMR analysis, a residual amount of about 0.05 mg of tetraglyme per g of product (I) was detected. The yield was 182.8 g, i.e. 98.8%.

EXAMPLE 4

The procedure was as in Example 1, but using 100 ml of tert-butyl methyl ether instead of diethyl ether. Using NMR analysis, residual amounts of about 0.54 mg of tertbutyl methyl ether and 0.14 mg of tetraglyme per g of product (I) were detected. The yield was 181.9 g, i.e. 98.3%.

EXAMPLE 5

The procedure was as in Example 1, but using a solution of 0.68 g of gaseous HCl in 100 ml of n-hexane (instead of a solution of chlorotrimethylsilane in diethyl ether). Using NMR analysis, a residual amount of about 0.04 mg of tetraglyme per g of product (I) was detected. The yield was 183 g, i.e. 98.9%.

EXAMPLE 6

8 kg of the HFPO crude oligomer contaminated with CsF, tetraglyme and F113 and having an average molecular weight of 5500 g/mol were introduced into a 10 l stirred round-bottom flask fitted with a drain tap. A solution of 28 g of chlorotrimethylsilane in 2000 ml of n-hexane was added to the crude oligomer and the mixture was stirred at room temperature for 90 minutes. After phase separation, the lower phase was drained off and filtered and freed from n-hexane and F113 under vacuum at 120° C. According to NMR analysis, the product (I) purified in this way still contained about 0.09 mg of tetraglyme per g of product (I). After filtration and distillation of the upper phase (n-hexane), 45 g (91%) of the tetraglyme used for the oligomerization and 35 g of CsCl (including the amount filtered off from the lower phase) were isolated.

The yield was 7350 g, i.e. 99.3%.

I claim:

1. A process for the preparation of perfluoropolyetheracyl fluorides of formula (I)

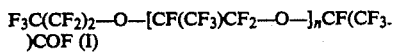

$F_3C(CF_2)_2-O-[CF(CF_3)CF_2-O-]_nCF(CF_3)COF$ (I)

in which n is an integer from 0–60, wherein hexafluoropropylene oxide is oligomerized in the presence of CsF and a polyethylene glycol dimethyl ether and the reaction mixture thus formed is reacted with at least one of the halogen compounds HCl, HBr, BCl$_3$, PCl$_3$, SCl$_2$ and R$_m$SiCl$_{4-m}$, where m=0, 1, 2 or 3 and R=C$_1$–C$_3$-alkyl or phenyl, dissolved in an aprotic solvent, and the resulting cesium halide precipitate is removed from the purified perfluoropolyetheracyl fluorides of formula (I).

2. The process as claimed in claim 1, wherein the halogen compound used is chlorotrimethylsilane or hydrogen chloride.

3. The process as claimed in claim 1, wherein the solvent used is n-hexane or cyclohexane.

4. The process as claimed in claim 2, wherein the solvent used is n-hexane or cyclohexane.

5. The process as claimed in claim 1, wherein n is an integer from 10 to 60.

6. The process as claimed in claim 4, wherein n is an integer from 10 to 60.

* * * * *